(12) United States Patent
Amthor et al.

(10) Patent No.: US 11,435,422 B2
(45) Date of Patent: Sep. 6, 2022

(54) ANOMALY DETECTION USING MAGNETIC RESONANCE FINGERPRINTING

(71) Applicant: KONINKLIJKE PHILIPS N.V., Eindhoven (NL)

(72) Inventors: Thomas Erik Amthor, Hamburg (DE); Mariya Ivanova Doneva, Hamburg (DE); Jan Jakob Meineke, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 31 days.

(21) Appl. No.: 17/027,743

(22) Filed: Sep. 22, 2020

(65) Prior Publication Data

US 2021/0003650 A1  Jan. 7, 2021

Related U.S. Application Data

(63) Continuation-in-part of application No. PCT/EP2019/056227, filed on Mar. 13, 2019.

(30) Foreign Application Priority Data

Mar. 22, 2018 (EP) ..................... 18163288

(51) Int. Cl.
*G01R 33/54* (2006.01)
*A61B 5/055* (2006.01)
(Continued)

(52) U.S. Cl.
CPC .......... *G01R 33/543* (2013.01); *A61B 5/055* (2013.01); *G01R 33/5608* (2013.01); *G06T 7/0012* (2013.01); *G06T 2207/20081* (2013.01)

(58) Field of Classification Search
CPC .. G01R 33/543; G01R 33/5608; A61B 5/055; G06T 7/0012
See application file for complete search history.

(56) References Cited

U.S. PATENT DOCUMENTS 8,520,923 B2  8/2013  Gindele et al.
9,633,455 B1  4/2017  Mailhe et al.
(Continued)

OTHER PUBLICATIONS

Dan Ma et al.,"Magnetic resonance fingerprinting" Nature Mar. 14, 2013 vol. 495 p. 187-193.
(Continued)

*Primary Examiner* — Dixomara Vargas

(57) ABSTRACT

The invention provides for a medical imaging system comprising: a memory for storing machine executable instructions; a processor for controlling the medical instrument. Execution of the machine executable instructions causes the processor to: receive MRF magnetic resonance data acquired according to an MRF magnetic resonance imaging protocol of a region of interest; reconstruct an MRF vector for each voxel of a set of voxels descriptive of the region of interest using the MRF magnetic resonance data according to the MRF magnetic resonance imaging protocol; calculate a preprocessed MRF vector (126) for each of the set of voxels by applying a predetermined preprocessing routine to the MRF vector for each voxel, wherein the predetermined preprocessing routine comprises normalizing the preprocessed MRF vector for each voxel; calculate an outlier map for the set of voxels by assigning an outlier score to the preprocessed MRF vector using a machine learning algorithm.

19 Claims, 8 Drawing Sheets

(51) Int. Cl.
*G01R 33/56* (2006.01)
*G06T 7/00* (2017.01)

(56) References Cited

U.S. PATENT DOCUMENTS

| | | | |
|---|---|---|---|
| 9,836,891 B2* | 12/2017 | Hatanaka | G06T 17/20 |
| 2005/0031210 A1* | 2/2005 | Shen | G06T 7/11 |
| | | | 382/215 |
| 2006/0229856 A1* | 10/2006 | Burrus | G16H 30/40 |
| | | | 703/11 |
| 2009/0306496 A1* | 12/2009 | Koo | A61B 5/055 |
| | | | 600/417 |
| 2010/0134491 A1 | 6/2010 | Borland et al. | |
| 2010/0166273 A1* | 7/2010 | Wismuller | G06T 19/00 |
| | | | 382/131 |
| 2012/0189178 A1* | 7/2012 | Seong | G06T 19/00 |
| | | | 382/128 |
| 2013/0034278 A1 | 2/2013 | Gindele et al. | |
| 2013/0131490 A1* | 5/2013 | Huston, III | G01R 33/56358 |
| | | | 600/410 |
| 2013/0231552 A1* | 9/2013 | Grady | A61B 5/055 |
| | | | 600/410 |
| 2015/0301141 A1 | 10/2015 | Griswold et al. | |
| 2015/0346301 A1 | 12/2015 | Cauley et al. | |
| 2016/0139227 A1 | 5/2016 | Grodzki et al. | |
| 2016/0328855 A1* | 11/2016 | Lay | G06K 9/4614 |
| 2016/0349341 A1 | 12/2016 | Cohen | |
| 2017/0007148 A1* | 1/2017 | Kaditz | A61B 5/055 |
| 2017/0011255 A1* | 1/2017 | Kaditz | G01R 33/48 |
| 2017/0100078 A1* | 4/2017 | Han | G01R 33/5608 |
| 2017/0103287 A1 | 4/2017 | Han | |
| 2017/0146623 A1 | 5/2017 | Cohen | |
| 2017/0160363 A1 | 6/2017 | Chen et al. | |
| 2017/0205482 A1 | 7/2017 | Zhao et al. | |
| 2017/0285122 A1* | 10/2017 | Kaditz | G01R 33/448 |
| 2017/0285123 A1* | 10/2017 | Kaditz | G01N 24/08 |
| 2017/0328973 A1 | 11/2017 | Amthor et al. | |
| 2017/0337687 A1* | 11/2017 | Wang | G06T 7/11 |
| 2018/0005381 A1 | 1/2018 | Patel et al. | |
| 2018/0139467 A1* | 5/2018 | Lee | G06T 7/20 |
| 2018/0321345 A1 | 11/2018 | Van Den Brink et al. | |
| 2018/0322635 A1* | 11/2018 | Guo | G06K 9/3233 |

OTHER PUBLICATIONS

Elisabeth Hoppe et al., Deep Learning for Magnetic Resonance Fingerprinting: A New Approach for Predicting Quantitative Parameter Values from Time Series; German Medidal Data Sciences 2017.
Eric Y. Pierre et al., Multiscale Reconstruction for MR Fingerprinting; Magnetic Resonance in Med. 75 p. 2481-2492 (2016).
International Search Report and Written Opinion from PCT/EP2019/056227 dated May 29, 2019.

* cited by examiner

ANOMALY DETECTION USING MAGNETIC RESONANCE FINGERPRINTING

CROSS REFERENCE TO RELATED APPLICATIONS

This application is a continuation-in-part of International Application No. PCT/EP2019/056227 filed on Mar. 13, 2019, which claims the benefit of EP Application Serial No. 18163288.6 filed on Mar. 22, 2018, each of which is incorporated herein by reference.

FIELD OF THE INVENTION

The invention relates to magnetic resonance imaging, in particular to magnetic resonance fingerprinting.

BACKGROUND OF THE INVENTION

Magnetic Resonance Fingerprinting (MRF) is a technique where a number of RF pulses, distributed in time, are applied such that they cause signals from different materials or tissues to have a unique contribution to the measured Magnetic Resonance (MR) signal. A limited dictionary of pre-calculated signal contributions from a set or fixed number of substances is compared to the measured MR signals. This can for example be used to determine intrinsic properties such as T1, T2, and B1+values. In other examples, the comparison between a dictionary of pre-calculated signals and the measured signal can be used to determining the material composition within a single voxel. For example, if it is known that a voxel only contains water, fat, and muscle tissue the contribution from these three materials need only be considered and intra-voxel component matching can be used to accurately determine the composition of the voxel. The magnetic resonance fingerprinting technique was introduced in the journal article Ma et al., "Magnetic Resonance Fingerprinting," Nature, Vol. 495, pp. 187 to 193, doi: 10.1038/nature11971.

SUMMARY OF THE INVENTION

One aspect of the invention provides for a medical imaging system, a computer program product, and a method as set forth in the independent claims.

Embodiments are given in the dependent claims.

As mentioned above, a dictionary of signals for a fixed number of substances is used in Magnetic Resonance Fingerprinting. If a particular substance is not within the dictionary, but is present within the subject being imaged then the matching to the dictionary could fail. This may result in errors in the calculation of the contents within a voxel. In this situation it is difficult to know if there is an abnormality within the subject, such as tumorous tissue, or if the preparation of the dictionary was insufficient.

Embodiments of the invention may provide for a way of identifying voxels that are abnormal without the prior preparation of an MRF dictionary. To do this, a machine learning algorithm is prepared. The machine learning algorithm is trained or prepared using MRF magnetic resonance data that is acquired from subjects who are not known to contain tissues that contains anomalies or abnormal anatomical structures. The machine learning algorithm is then used to calculate an outlier map for the MRF signal (also referred to as the MRF vector) for each voxel. The machine learning algorithm assigns an outlier score to each voxel. An outlier score is a numerical value which is a measure of how much the MRF vector being tested varies from the MRF vectors used to train or configure the machine learning algorithm.

The outlier map can then for example be displayed or rendered (possibly overlaid on other medical images) to help a healthcare professional identify voxels that produced abnormal or anomalous MRF vectors. This could be used to check the validity of a conventional MRF image, used for monitoring cancer growth, and/or for identifying regions of the subject to image or study further.

In one aspect the invention provides for a medical imaging system that comprises a memory for storing machine-executable instructions and a processor configured for controlling the medical instrument. The medical imaging system may take different forms in different examples. In some examples the medical imaging system is a system for processing or modifying images or data related to images. In other examples the medical imaging system may also comprise components for acquiring medical imaging data which is then processed or may be processed into data suitable for rendering.

In the case where the medical imaging system just comprises a memory and processor and possibly other normal components of a computer or workstation, controlling the medical instrument encompasses receiving processing and calculating data for generating data which is rendered or may be rendered into medical images. In other cases, the medical imaging system may comprise other components. The processor may therefore be configured for controlling these other components.

Execution of the machine-executable instructions causes the processor to receive MRF magnetic resonance data acquired according to an MRF magnetic resonance imaging protocol of a region of interest.

Execution of the machine-executable instructions further causes the processor to reconstruct an MRF vector for each voxel of a set of voxels descriptive of the region of interest using the MRF magnetic resonance data according to the MRF magnetic resonance imaging protocol. In magnetic resonance fingerprinting one or more parameters in a pulse sequence are varied and data in k-space is sampled. This sampled k-space data is then reconstructed into images. Instead of reconstructing the acquired magnetic resonance data directly into an image instead a series of images is produced. The value or values of a particular voxel for this series of images are then assembled into an MRF vector or a fingerprint for each voxel. The MRF vector may also be referred to as an MRF signal. In conventional magnetic resonance fingerprinting this MRF vector would then be compared to a dictionary comprising the MRF fingerprints or vectors for known substances or properties of the subject. In this embodiment the MRF vector which could be compared to a magnetic resonance fingerprinting dictionary is however processed differently.

Execution of the machine-executable instructions further cause the processor to calculate a pre-processed MRF vector for each of the set of voxels by applying a predetermined pre-processing routine to the MRF vector for each voxel. The predetermined pre-processing routine comprises normalizing the pre-processed MRF vector for each voxel.

In this execution by the processor the MRF vector for each voxel is calculated into a pre-processed MRF vector. The predetermined pre-processing routine is a routine which is used to standardize the MRF vector for each voxel. Execution of the machine-executable instructions further cause the processor to calculate an outlier map for the set of voxels by assigning an outlier score to the pre-processed MRF vector using a machine learning algorithm.

After the MRF vector has been processed by the predetermined pre-processing routine the resulting pre-processed MRF vector is then input into a machine learning algorithm. The output of this machine learning algorithm is an outlier map. An outlier map as used herein encompasses assigning a value to each voxel which represents how close the pre-processed MRF vector is to previous measurements which are considered to be normal. The outlier map is then a measure of how well the MRF vector for each voxel matches with expected values. This may have several advantages. Firstly, the outlier map can be used to indicate which regions of a subject should be more intensely evaluated or studied by a physician or other medical professional. This embodiment also has the advantage in that it is able to identify abnormalities in a magnetic resonance fingerprinting protocol that may not be identified otherwise. In conventional magnetic resonance fingerprinting it is mentioned before that the MRF vectors are compared to a magnetic resonance fingerprinting dictionary. The construction of this dictionary requires that relevant properties of a subject such as T1, T2 or other relaxation values or the concentrations of various compounds and substances are added to the dictionary. The use of a machine learning algorithm enables the identification of abnormal portions of a subject without having to use a magnetic resonance fingerprinting dictionary.

The outlier map may for example be stored for later use or it may be rendered or displayed in different ways on displays. The outlier map may also be used in a variety of ways. The outlier map could be used for planning further imaging protocols on a subject which may for example be conventional magnetic resonance imaging or even further magnetic resonance fingerprinting studies. The outlier map may be also useful for identifying abnormal regions of a subject for example for cancer screening or tracking the growth or remission of a cancer during therapy.

In another embodiment the medical imaging system further comprises a magnetic resonance imaging system. The memory further comprises MRF pulse sequence commands configured for controlling the magnetic resonance imaging system to acquire the MRF magnetic resonance data from the region of interest. The MRF pulse sequence commands are pulse sequence commands. The pulse sequence commands as used herein encompass commands or data which may be converted into commands that are used for controlling a magnetic resonance imaging system to acquire magnetic resonance data. In this example they are used for acquiring the MRF magnetic resonance data. The MRF magnetic resonance data is magnetic resonance data. The term MRF is used to specify particular magnetic resonance data.

The memory further comprises MRF pulse sequence commands configured for controlling the magnetic resonance imaging system to acquire the MRF magnetic resonance data from the region of interest. Execution of the machine-executable instructions further causes the processor to control the magnetic resonance imaging system to acquire the MRF magnetic resonance data. In this embodiment the medical imaging system comprises a magnetic resonance imaging system which is used to acquire the MRF magnetic resonance data.

In another embodiment execution of the machine-executable instructions further causes the processor to receive a segmentation of the voxels. The segmentation identifies a voxel type for each of the set of voxels. For example, the segmentation may identify the tissue type or organ type of particular voxels. The outlier score is at least partially assigned by using the voxel type as an input to the machine learning algorithm. In this embodiment the machine learning algorithm may be able to use the description of the voxels in the segmentation to further identify whether a particular voxel has what is considered a normal MRF vector. This may have the advantage of making the outlier map more accurate.

The segmentation of the set of voxels may take different examples in different forms. For example, the MRF magnetic resonance data may be used with a magnetic resonance fingerprinting dictionary to generate one or more MRF magnetic resonance images. These MRF magnetic resonance images may for example be segmented or the classification of the voxels using the magnetic resonance fingerprinting dictionary may also be used as input to the machine learning algorithm. In other examples a separately acquired conventional magnetic resonance image may be segmented and this segmentation may be used.

In another embodiment the voxel type is an anatomical location derived from an annotated anatomical atlas.

In another embodiment the voxel type is a tissue type.

In another embodiment the voxel type is an organ type.

In another embodiment the voxel type may be considered to be a so called global voxel. In the global voxel case there is no differentiation used. This may be combined with other results. For example, the outlier map may be calculated using the anatomical location, the tissue type, the organ type, and/or a global voxel designation. These different combinations of outlier maps may be combined to produce a weighted or global outlier map or may be screened individually. For example, an outlier map using the global voxel definition may in some instances not identify an abnormal voxel whereas when a segmentation is used and a particular organ type is identified for each voxel it may actually show that a voxel is abnormal for that particular type of organ but is normal in the global aspect.

In another embodiment execution of the machine-executable instructions further cause the processor to reconstruct a magnetic resonance image by reconstructing the magnetic resonance image from the MRF vector for each voxel using a magnetic resonance fingerprinting dictionary. Execution of the machine-executable instructions may also include optionally calculating the segmentation of the voxels from the reconstruction of the magnetic resonance image. This embodiment may be beneficial because a magnetic resonance image produced from magnetic resonance fingerprinting is generated and also the outlier map is provided. The outlier map may for example be superimposed or compared to the magnetic resonance imaging image. This may help in the interpretation of the magnetic resonance image and/or to guide a physician or other user of the magnetic resonance image to look at particular regions identified as being abnormal by the outlier map.

In another embodiment execution of the machine-executable instructions further cause the processor to reconstruct a magnetic resonance image by reconstructing the magnetic resonance image from imaging magnetic resonance data. The imaging magnetic resonance data is descriptive of the region of interest. For example, the memory may contain imaging magnetic resonance pulse sequence commands which are used to control the magnetic resonance imaging system to acquire the imaging magnetic resonance data. This embodiment may be beneficial because the outlier map could for example be thresholded and voxels above or below a particular value may be indicated on the magnetic resonance image. This may aid in the identification of abnormal anatomical regions of the subject or regions which should be imaged or studied further.

A magnetic resonance image as used herein encompasses an image which is generated from magnetic resonance data. In the above examples the magnetic resonance image was calculated either from the MRF vectors directly or from imaging magnetic resonance data. The magnetic resonance image may map single or multiple parameters. For example the magnetic resonance image could be a T1 weighted conventional magnetic resonance image or it could also be a T1 value calculated from the magnetic resonance fingerprinting vectors. In some examples the magnetic resonance image may comprise more than one value or a multidimensional signal for each particular voxel. The magnetic resonance image could then be rendered using different colors or schemes for showing the multidimensional signal.

In another embodiment execution of the machine-executable instructions further cause the processor to identify anomalous voxels by thresholding the outlier map. Execution of the machine-executable instructions further cause the processor to render a medical image comprising the magnetic resonance image. The anomalous voxels are marked in the medical image.

In another embodiment execution of the machine-executable instructions further cause the processor to modify the machine learning algorithm by receiving training MRF magnetic resonance data acquired according to an MRF magnetic resonance imaging protocol of a training region of interest. Execution of the machine-executable instructions further cause the processor to modify the machine learning algorithm by reconstructing a training MRF vector for each voxel of the set of training voxels descriptive of the training region of interest using the training MRF magnetic resonance data according to the MRF magnetic resonance imaging protocol.

Execution of the machine-executable instructions further cause the processor to modify the machine learning algorithm by calculating a training pre-processed MRF vector for each of the training set of voxels by applying the predetermined pre-processing routine to the MRF vector for each voxel. Execution of the machine-executable instructions further cause the processor to modify the machine learning algorithm by using the training pre-processed MRF vector to adapt variable parameters of the machine learning algorithm.

In another embodiment the predetermined pre-processing routine comprises reducing the dimensionality of the MRF vector for each voxel. The MRF vector comprises a component or value for each image that is acquired in the MRF magnetic resonance imaging protocol. It may be possible to reduce the dimensionality of the MRF vector by the predetermined pre-processing routine to simplify the calculation of the outlier map by the machine learning algorithm. This may have the benefit of decreasing the calculation time of the outlier map and/or improving the reliability of the outlier map.

In another embodiment the reduction of the dimensionality of the MRF vector for each voxel comprises applying a Fourier transform to the MRF vector and truncating the Fourier transformed MRF vector above a predetermined frequency value. For example the MRF vector may have several hundred different entries. The MRF vector can be Fourier transformed using a discreet Fourier transform and then essentially applying a low pass filter to it.

In another embodiment the reduction of the dimensionality of the MRF vector comprises condensing the MRF vector using a principal components analysis algorithm. This may be useful in eliminating components of the MRF vector which do not contain relevant information.

In another embodiment the reduction of the dimensionality of the MRF vector may comprise calculating multiple relaxation times using a magnetic resonance fingerprinting dictionary. For example, a particular combination of different relaxation times chosen from T1, T2, T2* or other relaxation times may be useful in identifying abnormal voxels.

In another embodiment the predetermined pre-processing routine comprises applying a mask to remove chosen voxels from the set of voxels. For example, if voxels are within a part of the imaging volume which does not contain any tissue it may not be useful or constructive to apply or calculate the outlier map there.

In another embodiment the predetermined pre-processing routine comprises deleting chosen voxels from the set of voxels if the MRF vector is below a predetermined amplitude or a predetermined measure. For example, if a particular voxel is on the boundary of a subject and does not contain a sufficient amount of tissue or other material it may not be useful to calculate the outlier map. In some embodiments both these above methods may be applied.

In another embodiment the trained machine learning algorithm is an outlier detection algorithm. An outlier detection algorithm is an algorithm that is configured for detecting how much a measurement deviates from other measurements so as to arouse suspicion that it is generated by a different mechanism or a different physical process. This may also be referred to as anomaly detection. The outlier detection algorithm may for example be a density-based technique such as the k nearest neighbor or a local outlier factor. Neural networks or various ensemble techniques or fuzzy logic may also be used.

In another embodiment the machine learning algorithm is an isolation forest algorithm.

In another embodiment the machine learning algorithm is a k-nearest neighbors' algorithm.

In another embodiment the machine learning algorithm is a one-class support vector machine algorithm.

In another embodiment, the predetermined preprocessing routine comprises calculating a spatially averaged MRF vector for a predetermined region surrounding each of the set of voxels. The predetermined preprocessing routine further comprises appending the spatially averaged MRF vector to the preprocessed MRF vector. These actions are performed by the processor. The predetermined region could for example be voxels within a predetermined distance of the voxel.

The predetermined region could also a region that was segmented. For example, the segmentation may be used to divide the voxels into regions which belong to different organs or tissue types. The spatially averaged MRF vector could be calculated for a particular tissue type or for a particular organ. The outlier map could then be used to detect anomalous voxels within a particular tissue type of organ. This may be useful in indicating abnormal anatomy or diseased tissue.

This embodiment may have the advantage that the outlier map is a combination of the MR finger print of each voxel as well as information about the spatial environment surrounding the voxel.

The addition of the averaged MRF vector to the preprocessed MRF vector enables the detection of unusual spatial variations as anomalies. When also combined with a voxel type, unusual spatial variations within specific organs or other segmented regions can also be detected.

In another embodiment, the predetermined preprocessing routine comprises calculating a spatial gradient MRF vector for each of the set of voxels. The predetermined preprocessing routine further comprises appending the spatially gradient MRF vector to the preprocessed MRF vector before calculating the outlier map. The spatial change of the MRF vector can also be used to detect anomalous voxels. This for example may be useful in detecting anomalous spatial changes in the MRF vector. As with the spatially averaged MRF vector, the voxel type may also be input into the machine learning algorithm. This may be useful in detecting abnormal or abrupt changes in the MRF vector.

In another aspect the invention provides for a computer program product comprising machine-executable instructions for execution by a processor. Execution of the machine-executable instructions causes the processor to receive MRF magnetic resonance data acquired according to an MRF magnetic resonance imaging protocol of a region of interest. Execution of the machine-executable instructions further causes the processor to reconstruct an MRF vector for each voxel the set of voxels descriptive of the region of interest using the MRF magnetic resonance data according to the MRF magnetic resonance imaging protocol.

Execution of the machine-executable instructions further causes the processor to calculate a pre-processed MRF vector for each of the set of voxels by applying a predetermined pre-processing routine to the MRF vector for each voxel. The predetermined pre-processing routine comprises normalizing the pre-processed MRF vector for each voxel. Execution of the machine-executable instructions further causes the processor to calculate an outlier map for the set of voxels by assigning an outlier score to the pre-processed MRF vector using a machine learning algorithm.

In another aspect the invention provides for a method of operating a medical imaging system. The method comprises receiving MRF magnetic resonance data acquired according to an MRF magnetic resonance imaging protocol of the region of interest. The method further comprises reconstructing an MRF vector for each voxel of the set of voxels descriptive of the region of interest using the MRF magnetic resonance data according to the MRF magnetic resonance imaging protocol. The method further comprises calculating a pre-processed MRF vector for each of the set of voxels by applying a predetermined pre-processing routine to the MRF vector for each voxel. The predetermined pre-processing routine comprises normalizing the pre-processed MRF vector for each voxel. The method further comprises calculating an outlier map to the set of voxels by assigning an outlier score to the pre-processed MRF vector using a machine learning algorithm.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins using the antenna of a Magnetic resonance apparatus during a magnetic resonance imaging scan. MRF magnetic resonance data is magnetic resonance data. Magnetic resonance data is an example of medical image data. A Magnetic Resonance Imaging (MRI) image or MR image is defined herein as being the reconstructed two or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF EMBODIMENTS

Like numbered elements in these figures are either equivalent elements or perform the same function. Elements which have been discussed previously will not necessarily be discussed in later figures if the function is equivalent.

Figure 1:
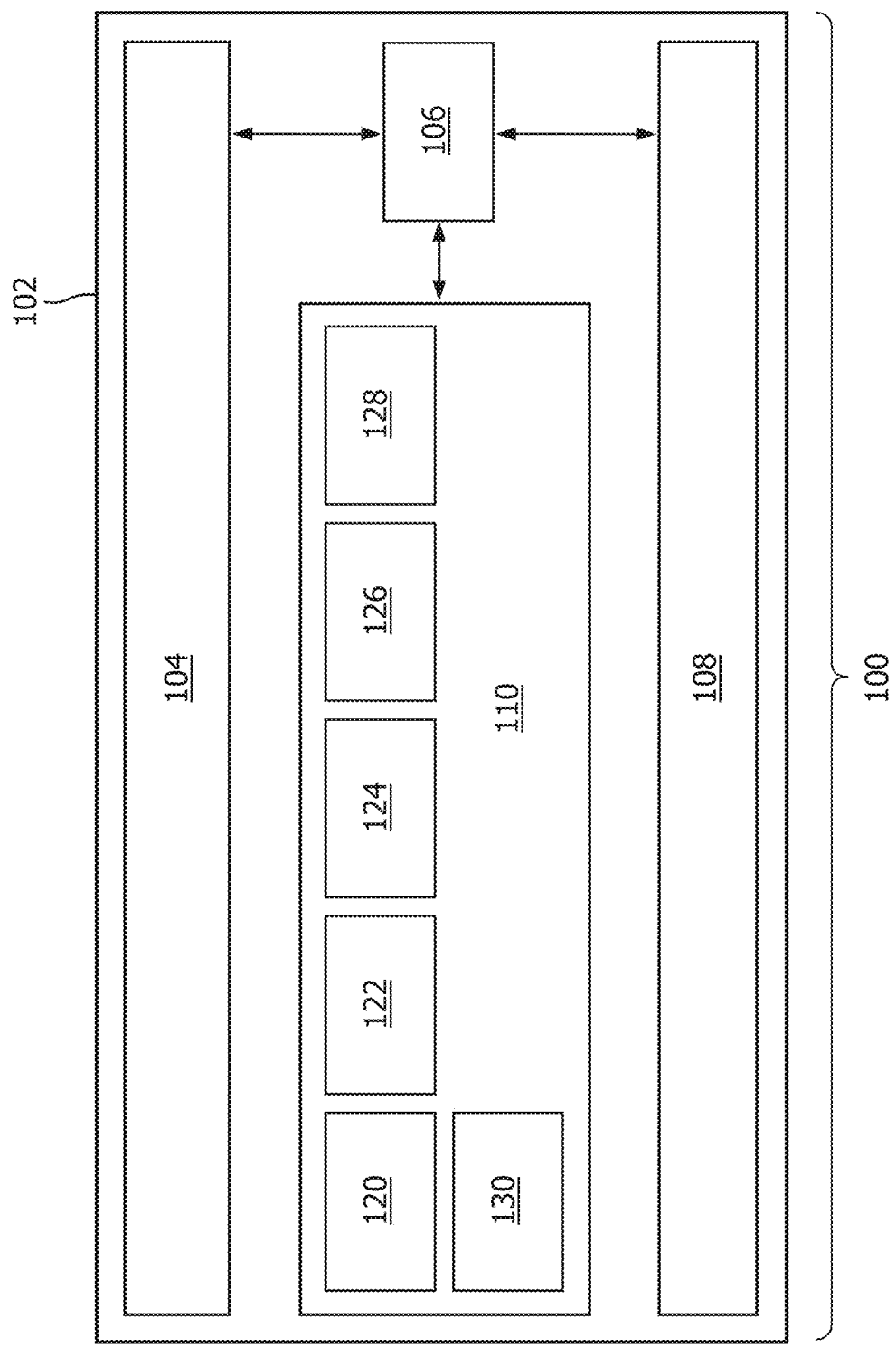
FIG. 1 illustrates an example of a medical imaging system.

FIG. 1 illustrates an example of a medical imaging system 100. The medical imaging system 100 of FIG. 1 comprises a computer 102. The computer 102 comprises a hardware interface or network interface 104 that is shown as being connected with a processor 106. The hardware interface or network interface 104 may for example be used for exchanging data with other computer systems or other components of the medical imaging system 100. For example, if the medical imaging system 100 were to comprise a magnetic resonance imaging system the hardware interface 104 could be used to send commands to control the magnetic resonance imaging system. The processor 106 is further shown as being connected to a user interface 108 and a memory 110. The memory 110 may be any combination of memory which is accessible to the processor 106. This may include such things as main memory, cached memory, and also non-volatile memory such as flash RAM, hard drives, or other storage devices. In some examples the memory 110 may be considered to be a non-transitory computer-readable medium.

The memory 110 is shown as containing machine-executable instructions 120. The machine-executable instructions 120 are commands which enable the processor 106 to perform various functions such as the control of other components of the medical imaging system 100 and to perform various numerical and data processing tasks. The memory 110 is further shown as containing MRF magnetic resonance data 122. The MRF magnetic resonance data 122 was acquired according to a magnetic resonance fingerprinting or MRF magnetic resonance imaging protocol and is descriptive of a region of interest. The memory 110 is further shown as containing an MRF vector for multiple voxels 124 that was calculated using the MRF magnetic resonance data 122. The memory 110 is further shown as containing a pre-processed MRF vector for multiple voxels 126. The pre-processed MRF vector for multiple voxels 126 was calculated using the MRF vector 124 for multiple voxels. The memory 110 is further shown as containing a machine learning algorithm 128. The machine learning algorithm 128 is able to take the pre-processed MRF vector for the multiple voxels 126 as input and is configured to output an outlier map 130. The outlier map 130 is also shown as being stored in the memory 110.

Figure 2:
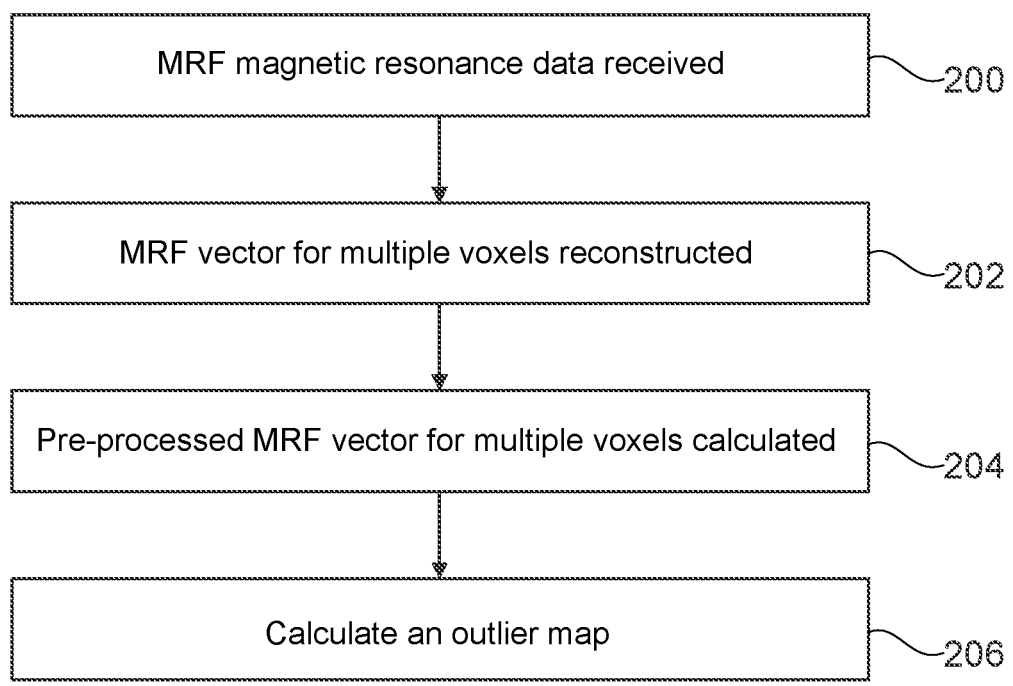
FIG. 2 shows a flow chart which illustrates a method of operating the medical imaging system of FIG. 1.

FIG. 2 shows a flowchart which illustrates a method of operating the medical imaging system 100 of FIG. 1. First in step 200 the MRF magnetic resonance data 122 is received. The MRF magnetic resonance data may for example be received via the network interface 104, via a storage medium connected to the computer 102 or it may also be acquired by a magnetic resonance imaging system controlled by the medical imaging system 100. Next in step 202 the MRF vector for multiple voxels 124 is reconstructed using the MRF magnetic resonance data 122 according to the MRF magnetic resonance imaging protocol. Next in step 204 the pre-processed MRF vector 126 for multiple voxels is calculated for each of the set of voxels by applying a predetermined pre-processing routine to the MRF vector 124 for each voxel. The predetermined pre-processing routine comprises at least normalizing the pre-processed MRF vector for each voxel. Finally, in step 206, the method comprises calculating an outlier map 130 for the set of voxels by assigning an outlier score to the pre-processed MRF vector 126 using the machine learning algorithm 128.

Figure 3:
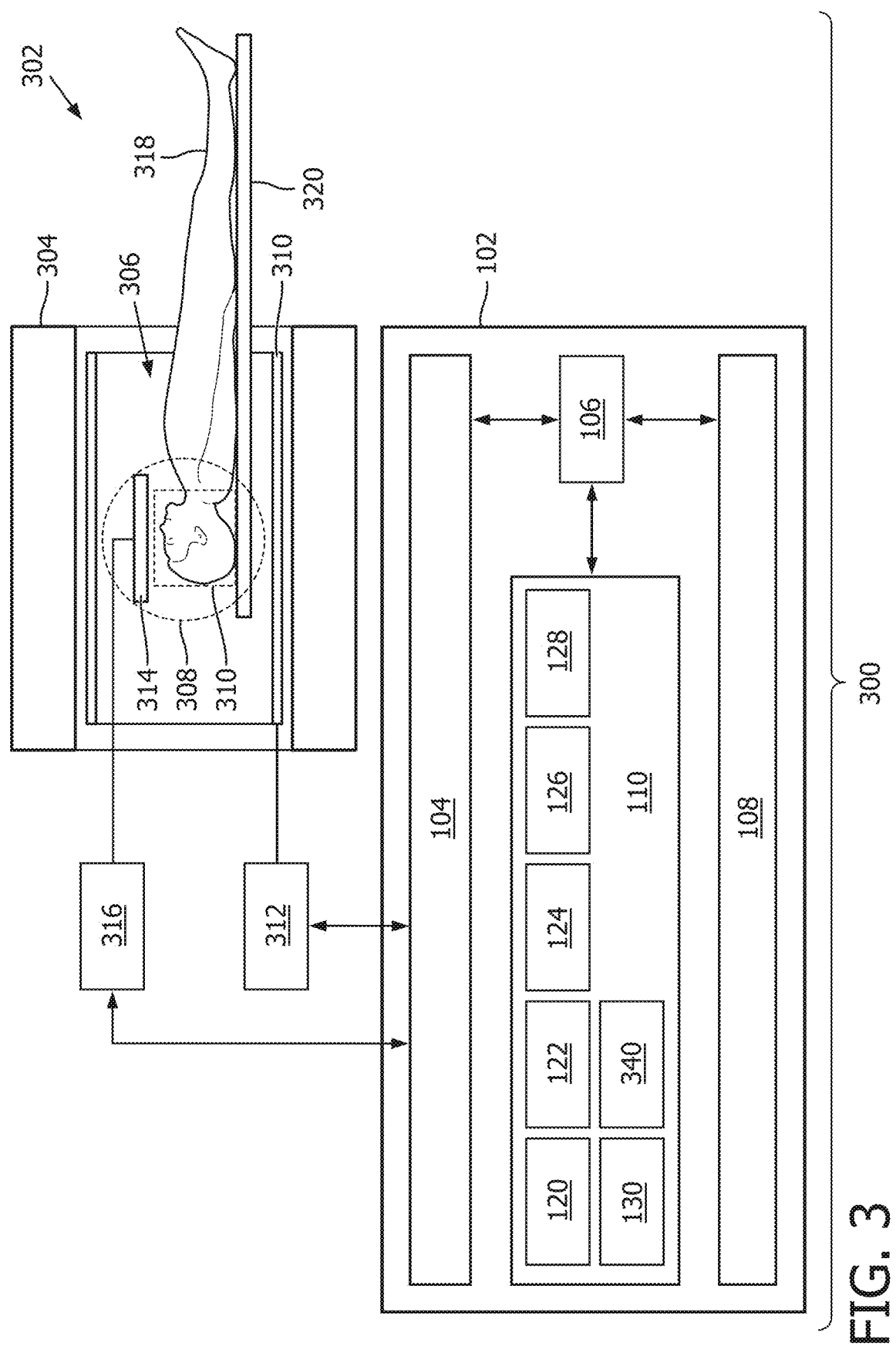
FIG. 3 illustrates a further example of a medical imaging system.

FIG. 3 illustrates a further example of a medical imaging system 300. In this example the medical imaging system further comprises a magnetic resonance imaging system 302. The magnetic resonance imaging system 302 comprises a magnet 304. The magnet 304 is a superconducting cylindrical type magnet with a bore 306 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 306 of the cylindrical magnet 304 there is an imaging zone 308 where the magnetic field is strong and uniform enough to perform magnetic resonance imaging. A region of interest 309 is shown within the imaging zone 308. A subject 318 is shown as being supported by a subject support 320 such that at least a portion of the subject 318 is within the imaging zone 308 and the region of interest 309.

Within the bore 306 of the magnet there is also a set of magnetic field gradient coils 310 which is used for acquisition of preliminary magnetic resonance data to spatially encode magnetic spins within the imaging zone 308 of the magnet 304. The magnetic field gradient coils 310 connected to a magnetic field gradient coil power supply 312. The magnetic field gradient coils 310 are intended to be representative. Typically magnetic field gradient coils 310 contain three separate sets of coils for spatially encoding in three orthogonal spatial directions. A magnetic field gradient power supply supplies current to the magnetic field gradient coils. The current supplied to the magnetic field gradient coils 310 is controlled as a function of time and may be ramped or pulsed.

Adjacent to the imaging zone 308 is a radio-frequency coil 314 for manipulating the orientations of magnetic spins within the imaging zone 308 and for receiving radio transmissions from spins also within the imaging zone 308. The radio frequency antenna may contain multiple coil elements. The radio frequency antenna may also be referred to as a channel or antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise the transceiver 316 may also represent a separate transmitter and receivers. The radio-frequency coil 314 may also have multiple receive/ transmit elements and the radio frequency transceiver 316 may have multiple receive/transmit channels. For example if a parallel imaging technique such as SENSE is performed, the radio-frequency coil 314 will have multiple coil elements.

In this example the subject, 318 is positioned such that the subject's head region is within the region of interest 309. In other examples, other parts of the subject's 318 body may be positioned in the region of interest 309.

The transceiver 316 and the gradient controller 312 are shown as being connected to the hardware interface 104 of the computer system 102. The memory 110 is further shown as containing MRF pulse sequence commands 340. The MRF pulse sequence commands 340 enable the processor 106 to control the magnetic resonance imaging system 302 to acquire the MRF magnetic resonance data 122.

Figure 4:
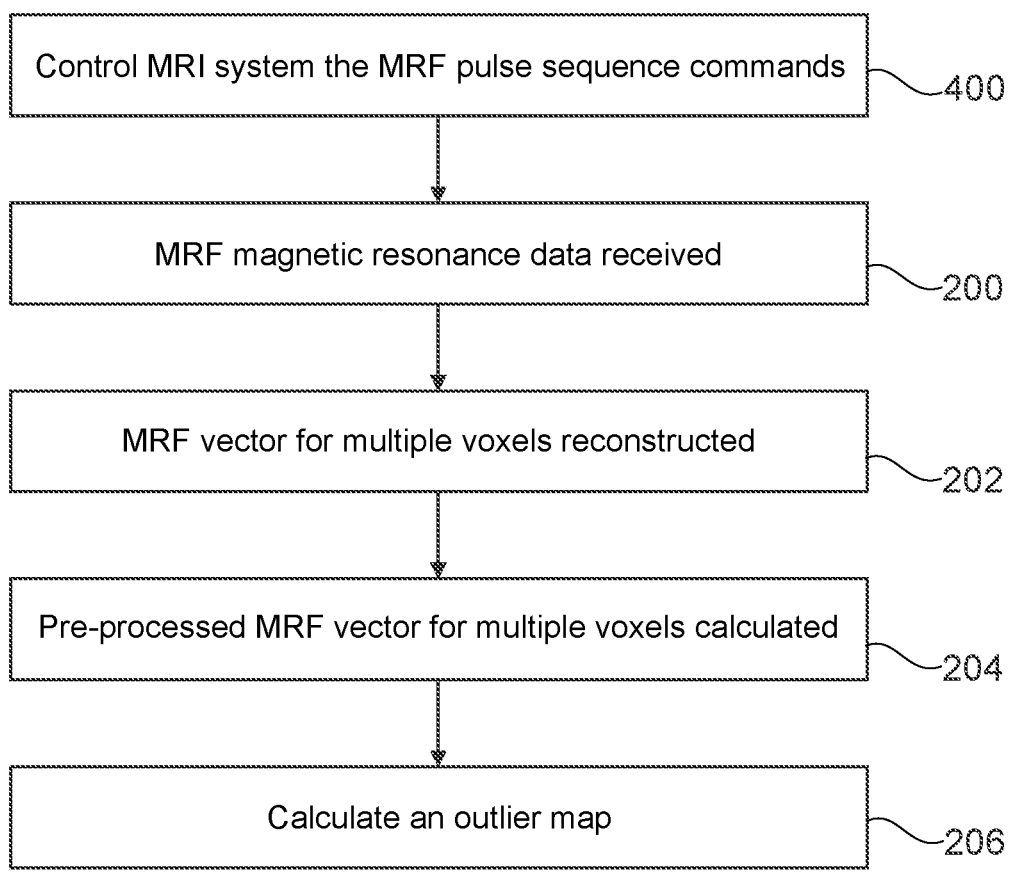
FIG. 4 shows a flow chart which illustrates a method of operating the medical imaging system of FIG. 3.

FIG. 4 shows a flowchart which illustrates a method of using the medical imaging system 300 of FIG. 3. The method starts with step 400. In step 400 the magnetic resonance imaging system 302 is controlled with the MRF pulse sequence commands 340 to acquire the MRF magnetic resonance data 122. The method then proceeds to step 200 as is illustrated in the flowchart of FIG. 2. The method of FIG. 4 then follows the method as is illustrated in FIG. 2.

Figure 5:
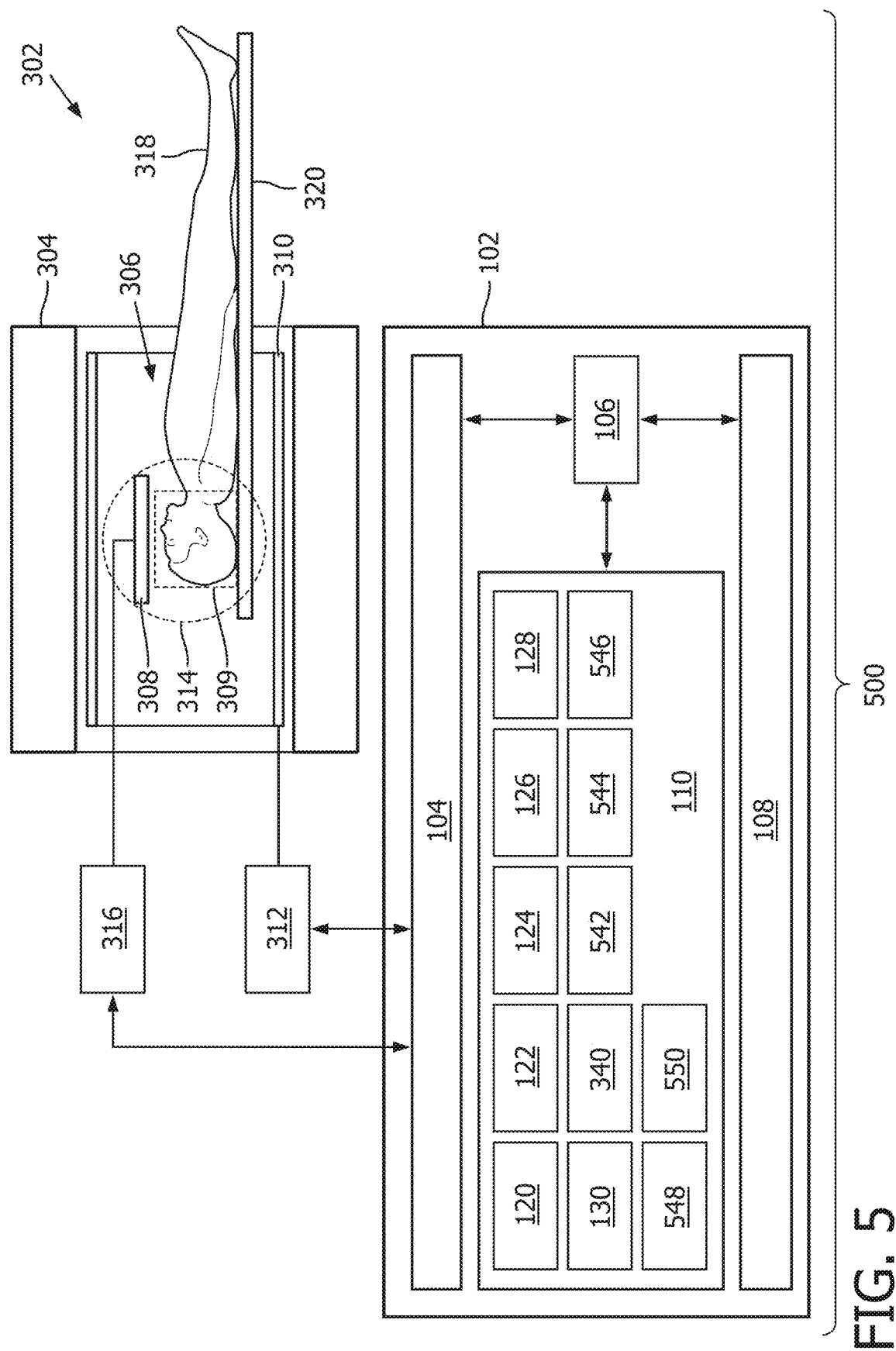
FIG. 5 illustrates a further example of a medical imaging system.

FIG. 5 shows a further example of the medical imaging system 500. The medical imaging system 500 is similar to the medical imaging system 300 in FIG. 3. The memory 110 of the medical imaging system 500 is shown as containing several additional items. The memory 110 is shown as additionally containing a magnetic resonance fingerprinting dictionary 542. The memory 110 is further shown as containing a magnetic resonance image 544 that was generated using the magnetic resonance fingerprinting dictionary 542 and the MRF magnetic resonance data 122 according to a conventional magnetic resonance fingerprinting imaging protocol.

The magnetic resonance image 544 in the memory 110 may therefore be considered a magnetic resonance fingerprinting magnetic resonance image. The memory 110 is further shown as containing an image segmentation 546 that was generated from the magnetic resonance image 544. The image segmentation 546 may for example assign a voxel type to each voxel of the MRF vector for the multiple voxels 124. The same is true for the pre-processed MRF vectors 126. The machine learning algorithm 128 may then take these voxel type identifications as a further input for determining the outlier map 130. The memory 110 is further shown as containing an identification of anomalous voxels 548 that was calculated by thresholding the outlier map 130. The memory 110 is further shown as containing a rendering of medical image 550 that is a combination of the identification of anomalous voxels 548 and the magnetic resonance image 544.

Figure 6:
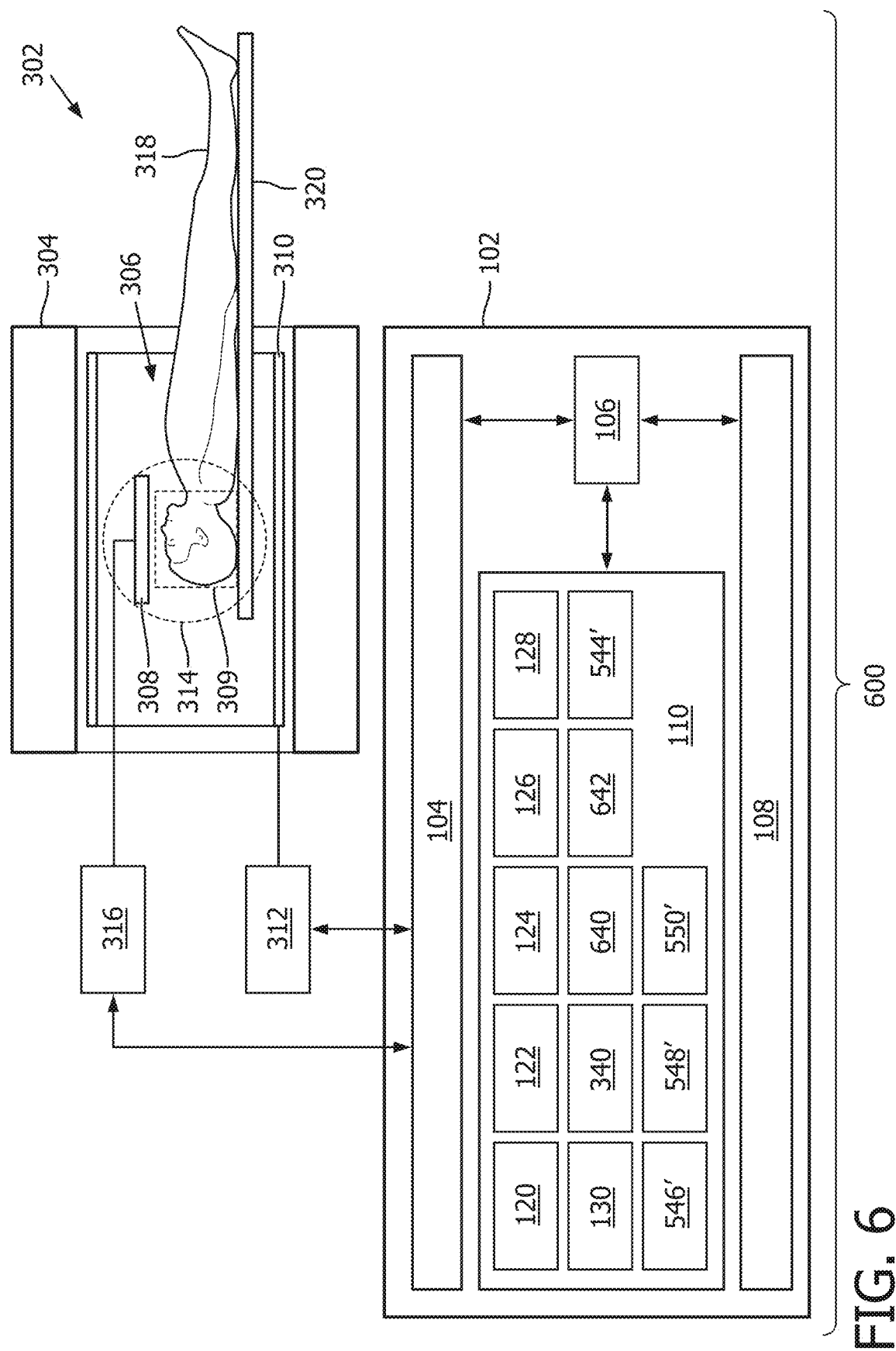
FIG. 6 illustrates a further example of a medical imaging system.

FIG. 6 illustrates a further example of a medical imaging system 600. The medical imaging system 600 in FIG. 6 is similar to the medical imaging system 300 in FIG. 3. The medical imaging system 600 has several additional items in its memory 110. The memory 110 is further shown as containing imaging pulse sequence commands 640. The imaging pulse sequence commands are instructions which enable the processor 106 to control the magnetic resonance imaging system to acquire imaging magnetic resonance data 642. The imaging pulse sequence commands 640 are according to a conventional magnetic resonance imaging protocol such as a T1, T2, or proton density weighted magnetic resonance imaging protocol. The imaging magnetic resonance data 642 may therefore be considered to be magnetic resonance data that was acquired according to a conventional magnetic resonance imaging protocol.

The memory 110 is further shown as containing a magnetic resonance image 544' that was reconstructed from the imaging magnetic resonance data 642. The memory 110 is further shown as containing an image segmentation 546' of the magnetic resonance image 544'. The memory 110 is further shown as containing an identification of anomalous voxels 548' that was made by thresholding the outlier map 130. The image segmentation 546' for example could have been used as input into the machine learning algorithm 128 to generate the outlier map 130. The memory 110 is shown as further comprising a rendering of a medical image 550' that combines the identification of anomalous voxels 548' and the magnetic resonance image 544'.

Multi-parametric MR images yield additional information about the tissue compared to a single MR contrast. MR Fingerprinting (MRF) can be considered a multi-dimensional imaging technique, since each fingerprint consists of a large number of data points. These are partly correlated, but still span a parameter space that may be larger than the two or three parameter dimensions known from standard multi-parametric imaging, depending on the number of parameters encoded in the MRF sequence.

Examples may overcome one or more of the following disadvantages:

Screening applications usually require knowledge about a specific clinical question, so that protocols can be selected and a radiologist can be asked to search for a specific pattern. Accordingly, screening applications will always be specific and require many resources.

Abnormalities in MRI are almost exclusively based on contrast changes in qualitative MR images and global changes in tissue properties cannot be detected.

Multi-parametric imaging, such as Magnetic Resonance Fingerprinting (MRF), may offer some more flexibility in producing contrasts, but usually still require prior information about what contrast to produce and, in the case of MRF, what signals to expect to construct a pre-calculated dictionary.

Examples may overcome these problems by proposing a way to detect irregularities and unusual features from multi-dimensional (MRF) image data. The evaluation can be performed either in a multi-dimensional parameter space (e.g. T1, T2, diffusion) or in a multi-dimensional feature space, which can be obtained by compressing the high dimensional MRF signal without explicitly extracting the physical tissue parameters before the processing. Without the need for a model accurately including all physical effects, the method allows to find and display unusual patterns in the images. This may serve as a computer-aided diagnostic tool, which can be applied in day to day diagnostic imaging, but also would benefit screening applications as well as follow up exams so that the radiologist can be made aware of regions in the images that may need closer investigation.

Examples may comprise one or more of the following features:

A setup for measuring MRF signals;

An algorithm to learn features of MRF signals and to calculate anomaly scores in a multi-dimensional feature space;

A method to calculate anomaly maps from measured MRF data;

A method to display anomaly maps, optionally in combination with other parameter maps.

As was previously mentioned, MRF is typically performed by matching the measured fingerprint signals to a pre-calculated dictionary. This requires the model underlying the dictionary calculation to be accurate and to include all physical effects associated with the imaging system and the subject. Once the tissue parameters are estimated, the proposed analysis can be performed on this multi-parametric data. (Actually also possible if the multi-parameter mapping is not MRF.) A limitation of the above mentioned approach is that it requires the dictionary to be complete with respect to the possible substances/tissue types, because otherwise unknown tissues will be mapped to (wrong) known ones. Detection of irregularities or unusual features of the investigated tissues is only possible when all of these requirements are met. Potential errors in the estimated tissue parameters may compromise the anomaly map.

The signal anomaly evaluation (calculation of an outlier map) can also be performed on the MRF temporal signals or any other multi-dimensional feature vector directly, without explicitly applying a signal model to extract the tissue parameters. This approach is at the core of some examples:

A machine learning algorithm is trained on healthy volunteer data to be able to measure how likely it is that a probe signal is normal or has some unusual irregularity. Without any knowledge of the underlying MR sequence or the clinical question, the resulting maps show a measure of how "normal" or "unusual" the tissue is.

Figure 7:
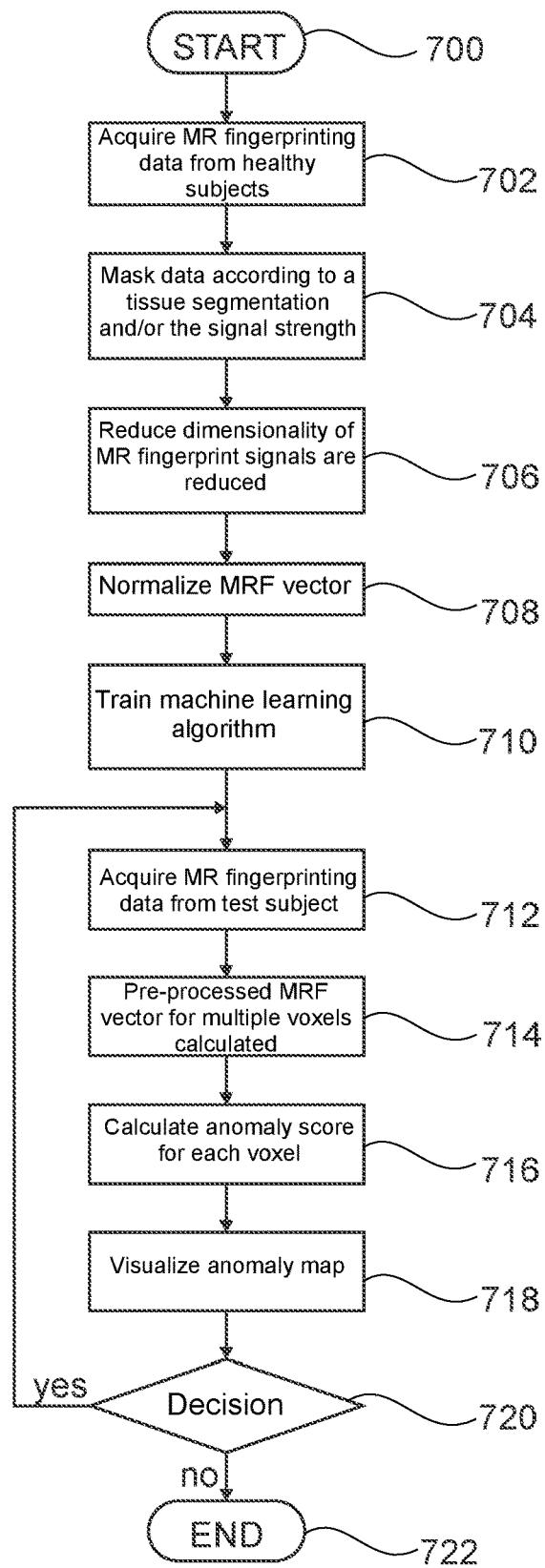
FIG. 7 shows a flow chart which illustrates an example of a method.

FIG. 7 shows a flowchart which illustrates an example of a method. The method starts with step 700 which is to start the method. Next in step 702 magnetic resonance fingerprinting data is acquired from healthy subjects. Step 704 is an optional step. In step 704 the data is masked according to a tissue segmentation and/or the signal strength. The data in step 704 is the MRF vector 124. Step 702 is equivalent to step 400 in FIG. 4. Step 706 is optional. In step 706 the dimensionality of the magnetic resonance fingerprint signals are reduced. Next in step 708 the MRF vector 124 is normalized. Steps 704, 706, and 708 are collectively equivalent to step 204 in FIG. 2. Next the method proceeds to step 710. In step 710 the machine learning algorithm which may also be referred to as the outlier detection algorithm is trained with the pre-processed MRF vectors 126 resulting from the application of steps 704, 706, and 708. Steps 702, 704, 706, 708 and 710 are collectively equivalent to a training or learning step for the machine learning algorithm. The steps after step 710 are equivalent to the methods illustrated in FIGS. 2 and 4.

After step 710 the method proceeds to step 712. In step 712 magnetic resonance fingerprinting data is acquired from a test subject. This is equivalent to step 400 of FIG. 4. The difference between steps 712 and 702 is that in step 702 the magnetic resonance fingerprinting data was acquired from what is known as a healthy or normal subject. It is expected that the data acquired in step 702 may contain no anomalies, very few anomalies, or a reduced number of anomalies. In step 712 it is unknown if the magnetic resonance fingerprinting data was acquired from a subject which has any anomalies in its anatomy. After step 712 the method proceeds to step 714. Step 714 is equivalent to step 204 in FIGS. 2 and 4. The steps performed in step 714 are equivalent and equal to the steps 704, 706, 708 that were performed earlier. Next in 716 an anomaly score is calculated for each voxel 716. Step 716 is equivalent to step 206. The anomaly score is equivalent to the outlier score. The method then proceeds to step 718. In step 718 the anomaly map, which may also be referred to as the outlier map, is visualized. Step 718 is optional. The outlier map or anomaly map may also be stored in a memory for later use. The method then proceeds to step 720. Step 720 is a decision box. The question is are there more subjects to process. If the answer is "no" then the method proceeds to step 722 and the method of FIG. 7 ends. If the answer is "yes" the method proceeds back to step 712 and steps 712, 714, 716, and 718 are performed again.

Preparation of training magnetic resonance data:

First, MRF data/multi-parametric MR data is acquired from several healthy subjects. Voxels to be included in the training data set are selected by signal amplitude (low-amplitude signals, e.g. outside the subject, are rejected) and optionally by tissue type (this can be achieved by calculating standard MRF classification maps, calculating standard MRF parameter maps and selecting a parameter range, manual segmentation, or automated model-based segmentation).

The signals selected as a training data set can optionally be compressed through dimensionality reduction. For example, in the case of spiral sampling (with periodically rotated spirals), a Fourier transform of the signals with subsequent selection of the low-frequency components can be used to eliminate sampling artefacts while maintaining most of the encoded tissue information.

The reduced signal vectors are still multi-dimensional and may span ten to several hundred dimensions.

The signals are then normalized to allow distance measures independent of the abundance of the substance in the voxel. Optionally, the vector elements may be transformed to absolute numbers to match the requirements of some machine-learning algorithms. Alternatively, the training data can be the estimated tissue parameters, T1, T2, proton density, diffusion, and/or other parameters.

Training of the machine learning algorithm:

Once the data set is prepared, a machine learning algorithm is trained or modified. Some example algorithms that can be used are:

The Isolation Forest algorithm:

This algorithm is well-suited for multi-dimensional cluster and outlier analysis. Once trained, it calculates a score for each test vector that specifies the conformity with the training data.

The k-NN (k nearest neighbors) algorithm:

For each test vector, this algorithm returns the distances to the k nearest neighbors from the training data set. In the context of some examples, the mean distance of the k nearest neighbors (with k=3 for example) would serve as a measure for the anomaly of the test vector.

The one-class support vector machine algorithm:

This algorithm uses a set of training examples to define a boundary between inliers and outliers. The test data points are then classified as belonging to one of two categories. This algorithm is an example of a non-probabilistic binary classifier that uses a model that assigns new examples to one category or the other.

Analysis of test data sets:

The signals measured from a test subject (patient to be screened) are prepared in the same way as the training signals (Voxel selection, dimensionality reduction, normalization).

The signals are then tested using the trained machine learning algorithm, which yields an anomaly score for each voxel.

Furthermore, the location of a voxel, e.g. frontal lobe, hippocampus, etc., could be taken into account for assessing the anomaly-score of a given signal. This can be achieved by warping the acquired data to an annotated atlas, e.g. using mesh-based image warping in combination with model-based segmentation.

Figure 8:
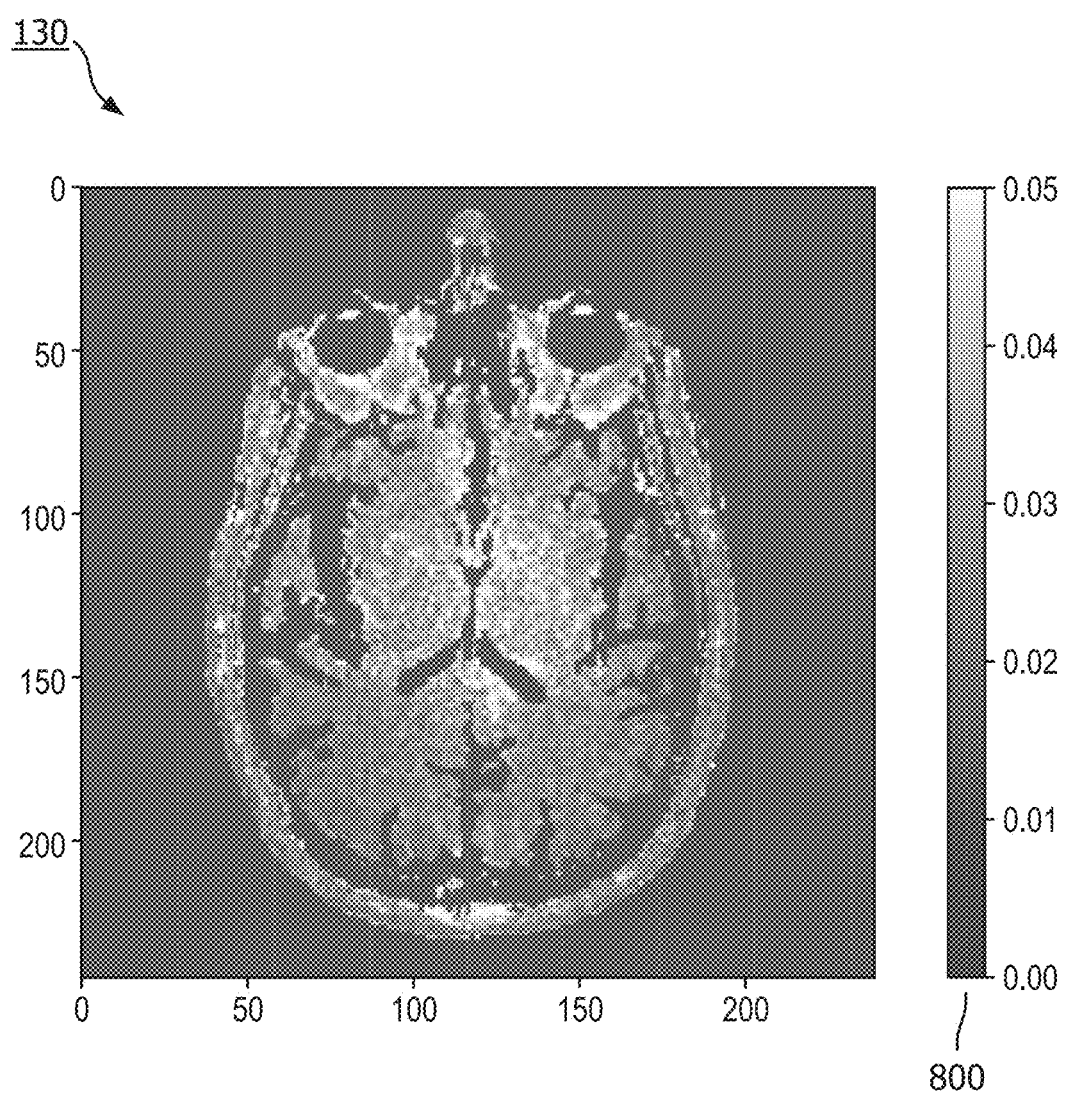
FIG. 8 shows an example of an outlier map.

FIG. 8 illustrates an example of an outlier map 130 which may also be referred to as an anomaly map. The FIG. 130 is a grayscale image which assigns an outlier score 800 to each voxel in the slice shown. The outlier score 800 is shown by the grayscale bar to the right of the image 130. The outlier score 800 may also be referred to by the term as anomaly score. The outlier or anomaly map of FIG. 8 was calculated using a 3-NN algorithm: Voxels containing liquids or very low signal have been excluded. The values indicate the mean distance of the MRF signal from the three closest nearest neighbors selected from the training data sets. In this case, this is the Euclidian distance of 30-dimensional normalized feature vectors. Since this is a healthy test subject, no significant anomalies are visible. This visualization could be overlaid, possibly in color, on standard contrast or parameter maps.

In another example, the anomaly maps are analyzed statistically or via image analysis to yield a proposal for the radiologist. This proposal could then be displayed as a marked image or a text, e.g. "High probability for irregularity in the frontal lobe region" or "Please check existence of lesions in region _____.".

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A medical imaging system comprising:
a memory for storing machine executable instructions;
a processor for controlling a medical instrument, wherein execution of the machine executable instructions causes the processor to:
receive MRF magnetic resonance data acquired according to an MRF magnetic resonance imaging protocol of a region of interest;
reconstruct an MRF vector for each voxel of a set of voxels descriptive of the region of interest using the MRF magnetic resonance data according to the MRF magnetic resonance imaging protocol;
calculate a preprocessed MRF vector for each of the set of voxels by applying a predetermined preprocessing routine to the MRF vector for each voxel, wherein the predetermined preprocessing routine comprises normalizing the preprocessed MRF vector for each voxel;
calculate an outlier map for the set of voxels by assigning an outlier score to the preprocessed MRF vector using a machine learning algorithm: and
receive a segmentation of the set of voxels, wherein the segmentation identifies a voxel type for each of the set of voxels, and wherein the outlier score is at least partially assigned by using the voxel type as an input to the machine learning algorithm.

2. The medical imaging system of claim 1, wherein the medical imaging system further comprises a magnetic resonance imaging system, wherein the memory further comprises MRF pulse sequence commands configured for controlling the magnetic resonance imaging system to acquire the MRF magnetic resonance data from the region of interest, wherein execution of the machine executable instructions cause the processor to control the magnetic resonance imaging system to acquire the MRF magnetic resonance data.

3. The medical imaging system of claim 1, wherein the voxel type is any one of the following: an anatomical location derived from an annotated anatomical atlas, a tissue type, an organ type, a global voxel, and combinations thereof.

4. The medical imaging system of claim 1, wherein execution of the machine executable instructions further causes the processor to reconstruct a magnetic resonance image according to any one of the following:
reconstruct the magnetic resonance image from the MRF vector for each voxel using a magnetic resonance fingerprinting dictionary; and
reconstruct the magnetic resonance image from imaging magnetic resonance data wherein the imaging magnetic resonance data is descriptive of the region of interest.

5. The medical imaging system of claim 4, wherein execution of the machine executable instructions further causes the processor to:
identify anomalous voxels by thresholding the outlier map; and
render a medical image comprising the magnetic resonance image, and wherein the anomalous voxels are marked in the medical image.

6. The medical imaging system of claim 5, wherein execution of the machine executable instructions further causes the processor to train the machine learning algorithm by:
receiving training MRF magnetic resonance data acquired according to an MRF magnetic resonance imaging protocol of a training region of interest;
reconstructing a training MRF vector for each voxel of a set of training voxels descriptive of the training region of interest using the training MRF magnetic resonance data according to the MRF magnetic resonance imaging protocol;
calculate a training preprocessed MRF vector for each of the training set of voxels by applying the predetermined preprocessing routine to the MRF vector for each voxel; and
train the machine learning algorithm using the training preprocessed MRF vector.

7. The medical imaging system of claim 6, wherein the trained machine learning algorithm is an outlier detection algorithm.

8. The medical imaging system of claim 1, wherein the predetermined preprocessing routine comprises reducing a dimensionality of the MRF vector for each voxel.

9. The medical imaging system of claim 8, wherein reducing the dimensionality of the MRF vector for each voxel comprises any one of the following:
  applying a Fourier transform to the MRF vector and truncating the Fourier transformed MRF vector above a predetermined frequency value;
  condensing the MRF vector using a principal components analysis algorithm; and
  calculating multiple relaxation times using an MRF dictionary.

10. The medical imaging system of claim 1, wherein the predetermined preprocessing routine comprises any one of the following:
  applying a mask to remove chosen voxels from the set of voxels;
  deleting the chosen voxels from the set of voxels if the MRF vector is below a predetermined amplitude or a predetermined measure; and
  combinations thereof.

11. The medical imaging system of claim 1, wherein the machine learning algorithm is any one of the following: an Isolation Forest algorithm, a k Nearest Neighbors algorithm, and a one-class support vector machine algorithm.

12. The medical imaging system of claim 1, wherein the predetermined preprocessing routine comprises:
  calculating a spatially averaged MRF vector for a predetermined region surrounding each of the set of voxels; and
  appending the spatially averaged MRF vector to the preprocessed MRF vector before calculating the outlier map.

13. The medical imaging system of claim 1, wherein the predetermined preprocessing routine comprises:
  calculating a spatial gradient MRF vector for each of the set of voxels; and
  appending the spatially gradient MRF vector to the preprocessed MRF vector before calculating the outlier map.

14. A computer program product comprising machine executable instructions stored on a non-transitory computer readable medium for execution by a processor, wherein execution of the machine executable instructions causes the processor to:
  receive MRF magnetic resonance data acquired according to an MRF magnetic resonance imaging protocol of a region of interest;
  reconstruct an MRF vector for each voxel of a set of voxels descriptive of the region of interest using the MRF magnetic resonance data according to the MRF magnetic resonance imaging protocol;
  calculate a preprocessed MRF vector for each of the set of voxels by applying a predetermined preprocessing routine to the MRF vector for each voxel, wherein the predetermined preprocessing routine comprises normalizing the preprocessed MRF vector for each voxel;
  calculate an outlier map for the set of voxels by assigning an outlier score to the preprocessed MRF vector using a machine learning algorithm, and
  receive a segmentation of the set of voxels, wherein the segmentation identifies a voxel type for each of the set of voxels, and wherein the outlier score is at least partially assigned by using the voxel type as an input to the machine learning algorithm.

15. The computer program product of claim 14, wherein the predetermined preprocessing routine comprises further executable instructions, which when executed by the processor, further cause the processor to:
  calculate a spatially averaged MRF vector for a predetermined region surrounding each of the set of voxels; and
  append the spatially averaged MRF vector to the preprocessed MRF vector before calculating the outlier map.

16. The computer program product of claim 14, wherein the predetermined preprocessing routine comprises further executable instructions, which when executed by the processor, further cause the processor to:
  calculate a spatial gradient MRF vector for each of the set of voxels; and
  append the spatially gradient MRF vector to the preprocessed MRF vector before calculating the outlier map.

17. The computer program product of claim 14, wherein the voxel type is any one of the following: an anatomical location derived from an annotated anatomical atlas, a tissue type, an organ type, a global voxel, and combinations thereof.

18. The computer program product of claim 14, wherein the execution of the machine executable instructions further causes the processor to reconstruct a magnetic resonance image according to any one of the following:
  reconstruct the magnetic resonance image from the MRF vector for each voxel using a magnetic resonance fingerprinting dictionary; and
  reconstruct the magnetic resonance image from imaging magnetic resonance data wherein the imaging magnetic resonance data is descriptive of the region of interest.

19. A method of operating a medical imaging system, wherein the method comprises:
  receiving MRF magnetic resonance data acquired according to an MRF magnetic resonance imaging protocol of a region of interest;
  reconstructing an MRF vector for each voxel of a set of voxels descriptive of the region of interest using the MRF magnetic resonance data according to the MRF magnetic resonance imaging protocol;
  calculating a preprocessed MRF vector for each of the set of voxels by applying a predetermined preprocessing routine to the MRF vector for each voxel, wherein the predetermined preprocessing routine comprises normalizing the preprocessed MRF vector for each voxel;
  calculating an outlier map for the set of voxels by assigning an outlier score to the preprocessed MRF vector using a machine learning algorithm; and
  receiving a segmentation of the set of voxels, wherein the segmentation identifies a voxel type for each of the set of voxels, and wherein the outlier score is at least partially assigned by using the voxel type as an input to the machine learning algorithm.

* * * * *